United States Patent [19]

Herd

[11] Patent Number: 4,929,757

[45] Date of Patent: May 29, 1990

[54] PROCESS FOR THE PREPARATION OF 3-AMINOPHENYL 2-HYDROXY-ETHYL SULPHONE

[75] Inventor: Karl-Josef Herd, Odenthal, Fed. Rep. of Germany

[73] Assignee: Bayer Aktiengesellschaft, Leverkusen, Fed. Rep. of Germany

[21] Appl. No.: 208,349

[22] Filed: Jun. 17, 1988

[30] Foreign Application Priority Data

Jun. 17, 1987 [DE] Fed. Rep. of Germany ....... 3720213

[51] Int. Cl.$^5$ .................. C07C 87/48; C07C 147/06; C07C 147/11; C07C 85/11
[52] U.S. Cl. ..................................... 564/423; 564/305
[58] Field of Search ............................... 564/305, 423

[56] References Cited

PUBLICATIONS

"Organosulfurchemistry", p. 692, Organic Chemistry, Allinger et al., 1971.
"Base–Catalyzed Cleavage of Epoxides", Cleavage of Epoxides, Nucleophilic Aromatic Substitution, pp. 567, 734, 826–828, Organic Chemistry, Morrison & Boyd, 1978.

*Primary Examiner*—John Kight, III
*Assistant Examiner*—Carlos Azpuru

[57] ABSTRACT

3-Aminophenyl 2-hydroxyethyl sulphone (I) can be prepared in a high yield and purity by treating 2-chloro-5-nitrophenyl 2-hydroxyethyl sulphone (II) or 4-chloro-3-nitrophenyl 2-hydroxyethyl sulphone (III) with hydrogen in the presence of hydrogenation catalysts in an aqueous or aqueous organic medium. (II) is obtained by reducing 2-chloro-5-nitrobenzenesulphochloride with sodium sulphite and subsequently reacting the product with ethylene oxide.

5 Claims, No Drawings

PROCESS FOR THE PREPARATION OF 3-AMINOPHENYL 2-HYDROXY-ETHYL SULPHONE

The present invention relates to a process for the preparation of the sulphone of the formula

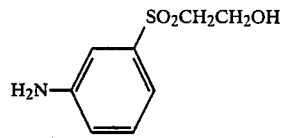

which is characterized in that a nitrosulphone of the formula

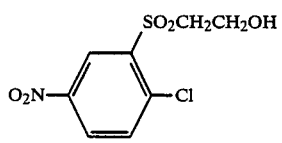

or

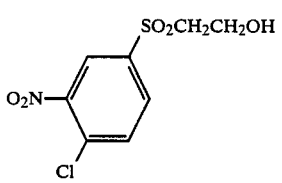

or a mixture of II and III is treated with hydrogen in the presence of hydrogenation catalysts.

The reaction is preferably carried out in an aqueous or aqueous organic medium, if appropriate in the presence of inert dispersants or emulsifiers.

Organic solvents suitable for this reaction are, in particular, water-miscible solvents, such as low-molecular aliphatic alcohols and ethers thereof, and also ethers such as dioxane and tetrahydrofuran. They are employed, if appropriate, in amounts of about 5 to 25% by weight.

The reaction is carried out at temperatures of about 40°–120° C., preferably 60°–80° C.

During the reaction the pH should be within the range from 5 to 8, preferably in the neutral range. This can be achieved by adding buffer substances, in particular phosphates, such as mixtures of primary, secondary and tertiary alkali metal phosphates, borates, acetates or alkali metal bicarbonates or alkali metal carbonates.

The required amount of buffer substances can readily be determined by preliminary tests. In the case of the alkali metal bicarbonates, it is appropriate to use equimolar amounts, relative to (II) or (III), respectively.

Examples of suitable hydrogenation catalysts are catalysts which consist of metals and/or compounds of elements of the eighth subgroup of the Periodic System of the elements according to Mendelyeev, or which contain the latter. The metals ruthenium, rhodium, palladium, platinum, cobalt and nickel and compounds thereof are preferred in this regard. The metal compounds can be, for example, oxides, hydroxides and/or hydrated oxides. The metals copper, vanadium, molybdenum, chromium and/or manganese and also compounds of these metals can be present in addition.

The hydrogenation catalysts can consist solely or mainly of substances which transfer hydrogen, but these catalysts can also be deposited on supporting materials. The following are examples of suitable supporting materials for the hydrogen-transferring substances: inorganic materials such as kieselguhr, silica, aluminium oxides, alkali metal and alkaline earth metal silicates, aluminium silicates, montmorillonite, zeolites, spinels, dolomite, kaolin, magnesium silicates, zirconium oxide, zinc oxide, calcium carbonate, silicon carbide, aluminium phosphate, boron phosphate, asbestos, active charcoal or barium sulphate, and also organic materials, for example naturally occurring or synthetic compounds of high molecular weight, such as silk, polyamides, polystyrenes, cellulose or polyurethanes. Inorganic supporting materials are preferred. The supporting material can be present, for example, in the form of spheres, extrudates, threads, cylinders, polygons or in the form of powder.

Supported catalysts of this type can, in general, contain 0.5 to 50% by weight, preferably 1 to 10% by weight, of the hydrogen-transferring substance, relative to the total weight of the supported catalyst. In this regard the hydrogen-transferring substance can be homogeneously distributed within the supporting material, but catalysts in which the hydrogen-transferring substance has been deposited in the outer layer or on the surface thereof are preferred. The preparation and the shaping of catalysts which can be used in the process according to the invention can be carried out in a known manner (see, for example, Houben-Weyl, Methoden der organischen Chemie ("Methods of organic chemistry"), volume IV, 1c, part I, pages 16–26, Georg Thieme-Verlag, Stuttgart, 1980).

Preferred supported catalysts are ruthenium on charcoal, ruthenium on aluminium oxide, rhodium on charcoal, rhodium on aluminium oxide, palladium on charcoal, palladium on aluminium oxide, palladium on calcium carbonate, palladium on barium sulphate, palladium on silica, platinum on charcoal and platinum on aluminium oxide.

Examples of preferred hydrogenation catalysts consisting solely or mainly of a hydrogen-transferring substance are oxide catalysts, such as palladium oxide, platinum oxide, ruthenium oxide and/or rhodium oxide/platinum oxide by Nishimura's method, and also black catalysts, such as palladium black, platinum black and rhodium black, which can be prepared by reducing corresponding metal salts or metal salt mixtures with alkali metal hydrides, alkali metal boranates, metal alkyls, hydrazine, formaldehyde, hydrogen or more electropositive metals.

Catalysts which are particularly preferred for the process according to the invention are palladium on charcoal, palladium on aluminium oxide, palladium on silica and palladium on calcium carbonate and also Raney nickel.

The amount of catalyst is generally about 0.1 to 10% by weight, preferably 0.1 to 5% by weight, relative to (II) or (III).

The hydrogen pressure is about 1 to 120 bar, preferably 5 to 40 bar.

The reaction time required for the process according to the invention depends on the reaction rate, the hydrogen partial pressure, the intensity with which the reaction mixture is mixed and the activity and concentration of the hydrogenation catalyst. In general, the reaction time necessary is within the range from 15 minutes up to several hours.

The catalytic activity of the hydrogenation catalysts is, in general, substantially retained when the process according to the invention is carried out, so that these catalysts can be employed repeatedly in the case of discontinuous procedure and can remain in use for a prolonged period in the case of continuous procedure.

In a simple discontinuous embodiment the process according to the invention can, for example, be carried out as follows: an autoclave capable of being thermostatically controlled and equipped with a stirring or mixing device is charged with the (II) or (III) to be employed, the hydrogenation catalyst and water or a water/solvent mixture. Hydrogen is then injected until the desired pressure is reached, and the mixture is heated to the desired reaction temperature with vigourous mixing. The progress of the reaction can be followed easily by measuring the consumption of hydrogen. Hydrogen consumed during the reaction can subsequently be metered in continuously or discontinuously. Th hydrogenation is discontinued when the desired amount of hydrogen has been taken up. The hydrogenation can be discontinued by cooling, terminating the mixing, releasing the pressure and/or removing the hydrogen atmosphere. The reaction mixture can, for example, be worked up by first filtering off the catalyst and concentrating the residual reaction solution and isolating, by filtering off with suction, the products which crystallize. The process according to the invention can also be carried out continuously.

The process can be carried out in one or two stages. In the two-stage process, the nitro group is fist reduced at about 40° C. in an aqueous medium, and reductive dehalogenation then carried out at above 50° C. after acid-binding buffer substances have been added. It is preferable to carry out the reaction in a single stage.

The present invention also relates to a process for the preparation of (I), characterized in that 2-chloro-5-nitrobenzenesulfochloride is reacted with sodium sulphite to give 2-chloro-5-nitrobenzenesulphinic acid, the latter is then reacted with ethylene oxide to give (II) and this is treated with hydrogen in the presence of hydrogenation catalysts.

Compared with the previously known process for the preparation of (I), namely converting 3-nitrobenzenesulphochloride into 3-nitrobenzenesulphinic acid, reacting the latter with ethylene oxide and subsequently reducing the nitro group, the process according to the invention exhibits the surprising advantage that it affords higher yields and a smaller amount of byproducts which are difficult to remove.

(I) is a valuable intermediate product for the preparation of dyestuffs. It is employed, for example, as a diazo component in the preparation of azo dyestuffs, in particular after being previously sulphated to give sulphatoethylsulphonylaniline.

EXAMPLE 1

Sodium 2-chloro-5-nitrobenzenesulphinate

The pH of a mixture of 1,000 g (3.8 moles) of a freshly prepared, approximately 40% strength aqueous solution of sodium bisulphite and 500 g of ice is adjusted to 7.5 by means of approximately 200 ml of concentrated sodium hydroxide solution. The mixture is cooled to 10° C. by adding approximately 400 g of ice. 1.47 kg (3.8 moles) of 2-chloro-5-nitrobenzenesulphonyl chloride in the form of a moist paste are introduced in portions at 10°–15° C. The temperature is kept constant by adding 1.6 kg of ice and the pH is kept constant at a value of 7–7.5 by adding 380 ml of sodium hydroxide solution. Stirring is continued subsequently until there is virtually no further change in the pH. The time required for the introduction and the subsequent stirring is about 4 hours. The pH is adjusted to 8.5 and 15 g of a customary filter aid are added. Clarification is carried out after a short period of further stirring, and the filter is rinsed with approximately 300 ml of water. The product is salted out with 1.3 kg of sodium chloride, the mixture is stirred for a further hour and the product is separated in a filter press. 1.35 kg of moist 2-chloro-5-nitrobenzenesulphinate are isolated. Analysis by HPLC gives a purity of 58.4%, which corresponds to a yield of 85% of theory. The product contains approximately 2% of 2-chloro-5-nitrobenzenesulphonate.

2-Chloro-5-nitrophenyl 2-hydroxyethyl sulphone 1,045 g (2.5 moles) of 2-chloro-5-nitrobenzenesulphinate in the form of a 58.4% strength moist paste and 1,250 ml of water are charged to a reaction vessel which has been flushed with nitrogen, and the pH is adjusted to a value between 7 and 8. The solution is heated to 60° C. under nitrogen. A total of 550 g of ethylene oxide is passed in slowly, the pH being kept meanwhile between 6 and 8 by metering in 25% strength sulphuric acid. A total of 1.02 kg of sulphuric acid is consumed. The reaction is complete after approximately 6–7 hours. Nitrogen is passed through the mixture for 1 hour at pH 7 and 85° C., and the latter is then cooled to room temperature. After stirring for 4 hours at 20° C., the precipitate is filtered off with suction and washed with twice 500 ml of water. This gives 775 g of moist paste or, after drying at 60 70° C. in vacuo, 602 g of 2-chloro-5-nitrophenyl 2-hydroxyethyl sulphone. According to C, H and N analysis and determination of nitro groups, chlorine and sulphur, the product is 98% pure, from which the yield is calculated to be 90.5% of theory.

3-Aminophenyl 2-hydoxyethyl sulphone 271 g (1 mole) of the above 2-chloro-6-nitrophenyl 2-hydroxyethyl sulphone are stirred into 1.8 l of water in a 3 l autoclave, and 85 g of solid sodium bicarbonate and 1 ml of an emulsifier (polyether based on lauryl alcohol and ethylene oxide) are added. The mixture is heated to 70° C. 20 g of Raney nickel, freshly prepared from a 50:50 aluminium/nickel alloy, are added and hydrogen is injected to approximately 40 bar. At a reaction temperature of 70°–75° C., the hydrogen pressure is kept within the range between 20 and 25 bar. An additional rise in pressure as the result of $CO_2$ being liberated should be taken into account. When, after approximately 2–3 hours, the consumption of hydrogen declines markedly, a sample is withdrawn and examined by chromatography (silica gel on aluminium foil; eluant: 1:1 acetone/ligroin) to check the completeness of dehalogenation. When the reaction is complete, the pressure in the autoclave is released, the latter is flushed with nitrogen and the warm reaction mixture is clarified via a pressure filter, the catalyst being retained as a residue on the filter.

The filtrate is concentrated on a rotary evaporator at 60° C./20 mm Hg. The resulting 263 g of an oil which contains sodium chloride and which solidifies in a crystalline state on cooling to 0°–5° C. prove to contain virtually only the single substance 3-aminophenyl 2-hydroxyethyl sulphone. According to determination of content, the product is approximately 71% strength, which corresponds to a yield of 93% of theory.

EXAMPLE 2

34.2 g of moist paste of 2-chloro-5-nitrophenyl 2-hydroxyethyl sulphone from Example 1 [or an equimolar amount of 4-chloro-3-nitrophenyl 2-hydroxyethyl sulphone]are stirred into 250 ml of water and 50 ml of a phosphate buffer solution which has been prepared by dissolving 0.5 mole of disodium phosphate and 0.33 mole of monosodium phosphate in 1 l of water. When 1-2 g of a nonionic emulsifier and 1.5 g of Raney nickel, prepared from a 70:30 aluminium-nickel alloy, have been added, the mixture is heated to 80° C. Hydrogen is then injected to 20 bar. The subsequent feed of hydrogen is controlled at such a rate that the pressure is constant at 10-15 bar. When the consumption of hydrogen declines markedly, a sample is withdrawn and examined by chromatography (see Example 1) to check the completeness of the reduction. If, in a given case, 5-amino-2-chlorophenyl 2-hydroxyethyl sulphone [or 3-amino-4-chlorophenyl 2-hydroxyethyl sulphone] is still detectable, approximately 0.5-1.0 g more catalyst is added and hydrogenation is carried out again at 80° C. and 20 bar. When the reduction and dehalogenation are complete, the pressure in the autoclave is released and the latter is flushed with nitrogen, and the catalyst is removed from the warm reaction solution by suction filtration. The solution is cooled and acidified with hydrochloric acid, and the content of 3-aminophenyl 2-hydroxyethyl sulphone in the solution is determined by diazotization with 10% strength sodium nitrite solution. The yield is approximately 90% of theory. The solution of 3-aminophenyl 2-hydroxyethyl sulphone thus obtained can be processed further directly in this form; it can, for example, be diazotized and the diazonium salt solution can be coupled, as described in Japanese Patent Application No. 05,667/70, with 7-acetylamino-1-naphthol-3-sulphonic acid.

EXAMPLE 3

102.6 g of moist paste of 2-chloro-5-nitrophenyl 2-hydroxyethyl sulphone from Example 1 [or an equimolar amount of 4-chloro-3-nitrophenyl 2-hydoxyethyl sulphone] are stirred into 250 ml of water and 50 ml of the phosphate buffer solution described under Example 2. A small amount of a nonionic emulsifier and 5 g of palladium-oncharcoal catalyst are added. Hydrogenation with hydrogen is then carried out in an autoclave at 70° C. and approximately 40 bar. The reduction is monitored by chromatography. After the hydrogenation, and after releasing the pressure and flushing the reactor, the product is heated to 85° C. and clarified via a pressure filter. The filter is cooled to 0° C. and the crystalline 3-aminophenyl 2-hydroxyethyl sulphone is isolated by filtration. 53 g of single-substance product are obtained after drying.

I claim:

1. A process for the preparation of the sulphone of the formula

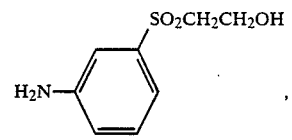

wherein 2-chloro-5-nitrobenzenesulphochloride is reacted with sodium sulphite to give 2-chloro-5-nitrobenzenesulphinic acid, the benzenesulphinic acid product is then reacted with ethylene oxide to give 2-chloro-5-nitrophenyl hydroxyethyl sulphone and the latter is then treated with hydrogen in the presence of hydrogenation catalysts to form the sulphone.

2. Process according to claim 1, wherein the hydrogenation reaction is carried out in an aqueous or aqueous organic medium.

3. Process according to claim 1, wherein the hydrogenation reaction is carried out at temperatures of about 40° to 120° C. and pH values of 5 to 8.

4. Process according to claim 1, wherein the hydrogenation catalysts used are nickel catalysts or Pd supported catalysts.

5. Process according to claim 4, wherein the metal catalyst is Raney nickel.

* * * * *